United States Patent [19]
Bertolini et al.

[11] Patent Number: 6,034,096
[45] Date of Patent: Mar. 7, 2000

[54] COMPOUNDS WITH ANTI-INFLAMMATORY AND IMMUNOSUPPRESSIVE ACTIVITIES

[75] Inventors: Giorgio Bertolini; Mauro Biffi; Flavio Leoni; Jacques Mizrahi; Gianfranco Pavich; Paolo Mascagni, all of Cinisello Balsamo, Italy

[73] Assignee: Italfarmaco S.p.A., Milan, Italy

[21] Appl. No.: 09/180,606

[22] PCT Filed: May 12, 1997

[86] PCT No.: PCT/EP97/02407

§ 371 Date: Nov. 12, 1998

§ 102(e) Date: Nov. 12, 1998

[87] PCT Pub. No.: WO97/43251

PCT Pub. Date: Nov. 20, 1997

[30] Foreign Application Priority Data

May 14, 1996 [IT] Italy ................................ MI96A0968

[51] Int. Cl.[7] ...................... C07C 259/08; C07C 259/10; C07D 217/00; A61K 31/47
[52] U.S. Cl. ......................... 514/307; 514/575; 546/146; 546/147; 558/233; 560/132; 560/133
[58] Field of Search ............................... 561/32; 560/132, 560/133; 546/146, 147; 514/307, 575; 558/233

[56] References Cited

U.S. PATENT DOCUMENTS

| | | | |
|---|---|---|---|
| 2,800,498 | 7/1957 | Chabrier et al. | 514/46 |
| 4,314,936 | 2/1982 | Yaron et al. | 514/46 |
| 4,711,900 | 12/1987 | Varma et al. | 560/8 |
| 5,280,015 | 1/1994 | Jacobson et al. | 514/46 |

FOREIGN PATENT DOCUMENTS

| | | |
|---|---|---|
| 310 720 | 10/1973 | Austria . |
| 311 939 | 12/1973 | Austria . |
| 0 196 674 | 10/1986 | European Pat. Off. . |
| 0 261 759 | 3/1988 | European Pat. Off. . |
| 2 354 315 | 1/1978 | France . |
| 267 978 | 5/1989 | German Dem. Rep. . |

OTHER PUBLICATIONS

Patent Abstracts of Japan, vol. 5, No. 132 (C–68) [804], Aug. 22, 1981 & JP 56 068650 A, Otsuka Seiyaku K.K., Jun. 9, 1981.

Fuji et al., Chemical Abstracts, vol. 87, No. 5, Abstract No. 39,013, col. 2, Aug. 1, 1977.

*Primary Examiner*—Zinna Northington Davis
*Attorney, Agent, or Firm*—Griffin, Butler, Whisenhunt & Szipl, LLP

[57] ABSTRACT

The present invention provides medicinal compounds that are characterized by a cyclic moiety (A) linked through a carboxamido group (more specifically, a carbamate group or a urea group) to another cyclic moiety (B) which is in turn linked to another, N-substituted carboxamido group. These compounds can be used an anti-inflammatory and immunosuppressive agents, as demonstrated by their inhibition of the production of IL-1β in vitro and TNFα in vivo.

15 Claims, No Drawings

COMPOUNDS WITH ANTI-INFLAMMATORY AND IMMUNOSUPPRESSIVE ACTIVITIES

This application is a 371 of PCT/EP97/02407 filed May 12, 1997.

The present invention relates to novel compounds and the use thereof as anti-inflammatory and immunosuppressive agents.

The role of cytokines (such as IL-1β and α, TNFα and IL-6) in the development of inflammatory reactions is well known (Dinarello C. A. and Wolff S. M., New Eng. J. Med. 328(2): 106113, 1993; Tracey K. J. and Cerami A., Crit. Care Med. 21: S415, 1993; Melli M. and Parente L., Cytokines and lipocortins in inflammation and differentiation. Wiley-Liss. New York 1990; Dawson M. M. Lymphokines and Interleukins. CRC Press. Boca Raton, Fla. 1991). A great number of searches have been carried out in order to find compounds, named cytokine suppressive anti-inflammatory drugs (CSAID), exerting an inhibitory effect on the production of pro-inflammatory cytokines, particularly IL-1β and TNFα (Lee J. C. et al., Nature 372: 739, 1994; Davidsen S. K. and Summers J. B., Exp. Opin. Ther. Patents. 5(10): 1087, 1995), and recently wide-spectrum agents named non-traditional non-sterodial anti-inflammatory drugs have been disclosed (Chiou G. C. Y. and Liu S. X. L., Exp. Opin. Ther. Patents. 6(1): 41,1996).

Tanaka et al., Chem. Pharm. Bull., 31(8), 2810–2819 (1983) report the importance of the hydroxamic group for the antiinflammatory activity: it is said to have such a paramount role as to overshadow the other parts of the molecule, wherein groups such as the methoxy one can increase the inflammatory potency, whereas other groups, such as the acetamido one, cause a decrease in the activity.

Now it has surprisingly been found that hydroxamic acid derivatives containing an amidobenzoic moiety exert, contrary to what reported in the prior art, a remarkable antiinflammatory action, together with an immunosuppressive activity.

Therefore the present invention relates to compounds of formula (I):

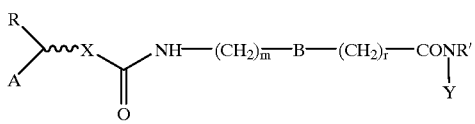

wherein R' is hydrogen or $(C_{1-4})$alkyl;

A is adamantyl or a mono-, bi- or tricyclic residue optionally partially or totally unsaturated, which can contain one or more heteroatoms selected from the group consisting of N, S or O and optionally substituted by hydroxy, alkanoyloxy, primary, secundary or tertiary amino, amino$(C_{1-4})$alkyl, mono- or di$(C_{1-4})$alkyl-amino$(C_{1-4})$alkyl, halogen, $(C_{1-4})$alkyl, tri$(C_{1-4})$ alkylammonium$(C_{1-4})$ alkyl;

∿∿∿ is a chain of 1 to 5 carbon atoms optionally containing a double bond or a NR' group wherein R' is as defined above;

R is hydrogen or phenyl;

X is a oxygen atom or a NR' group wherein R' is as defined above, or is absent;

r and m are independently 0, 1 or 2;

B is a phenylene or cyclohexylene ring;

Y is hydroxy or an amino$(C_{1-4})$alkyl chain optionally interrupted by an oxygen atom;

with the proviso that a tricyclic group as defined for A is fluorenyl only when at the same time X is different from 0 and Y is different from hydroxy, unless said fluorenyl is substituted by a tri$(C_{1-4})$alkylammonium $(C_{1-4})$alkyl group.

As hereinbelow meant, an alkyl group as defined above is, for example, methyl, ethyl, 2-methylethyl, 1,3-propyl, 1,4-butyl, 2-ethylethyl, 3-methylpropyl, 1,5-pentyl, 2-ethylpropyl, 2-methylbutyl and analogues, whereas a mono-, bi or tricyclic group as defined above can be phenyl, cyclohexyl, pyridyl, piperidyl, pyrimidyl, pyridazyl, naphthyl, indenyl, anthranyl, phenanthryl, fluorenyl, furanyl, pyranyl, benzofuranyl, chromenyl, xanthyl, isothiazolyl, isoxazolyl, phenothiazyl, phenoxazyl, morpholyl, thiophenyl, benzothiophenyl and the like. A halogen atom can be chlorine, bromine or fluorine. Finally, by alkanoyloxy group, acetyloxy, propionyloxy, ipropionyloxy, butanoyloxy and similar are meant.

A first group of preferred compounds of formula I are those wherein R' is hydrogen; A is selected from phenyl, 1- or 2- naphthyl, cyclohexyl, 1- or 2- 1,2,3,4-tetrahydronaphthyl, adamantyl, quinolinyl, isoquinolinyl, 1- or 2- indenyl, tetrahydroquinolinyl, tetrahydroisoquinolinyl optionally substituted as mentioned above;

∿∿∿ is a $C_1$–$C_5$, preferably $C_1$–$C_3$, chain, such as a methylene, ethylene, propylene or propenyl group;

Y is OH and R, B, m and r are as defined above.

A second group of preferred compounds are those wherein R' is hydrogen; A is optionally substituted phenyl or 1- or 2- naphthyl, more preferably 1- or 2- naphthyl; R is phenyl when A is phenyl, or is hydrogen when A is 1- or 2-naphthyl; R, B, m and r are as defined above; Y is OH and the $C_1$–$C_3$ alkylene chain is as defined above for the first group of preferred compounds.

The A groups are preferably substituted by a $(C_1$–$C_4)$-alkylamino$(C_1$–$C_4)$-alkyl group.

A further object of the invention relates to the use of the compounds of formula (I) as anti-inflammatory and immunosuppressive agents, and the incorporation thereof in pharmaceutical compositions including pharmaceutically acceptable excipients.

The compounds of the invention are prepared according to procedures known to those skilled in the art. The starting compounds used for this preparation are commercially available compounds or can be prepared according to literature.

A compound of formula (I) in which X is present is prepared starting from a compound of formula (II)

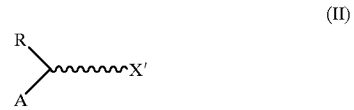

wherein R and A are as defined above, and X' is an oxygen atom or a NR' group, wherein R' is as defined above. This compound is reacted with a carbonic acid reactive derivative such as disuccinimidyl carbonate or carbonyl diimidazole (CDI), in the presence of a tertiary amine, such as triethylamine, or an aromatic one, such as pyridine, in inert solvents such as acetonitrile, tetrahydrofuran (THF), dioxane, chlorinated solvents, at a temperature from room temperature to the solvent's reflux one and for times ranging from about 1 to about 48 hours.

The resulting compound (III)

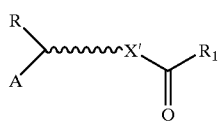

(III)

wherein R, A and X' are as defined above, and R₁ is an imidazolyl or hydroxysuccinimidyl group, is reacted with the desired amino acid in a mixture of water and a water-miscible organic solvent, such as tetrahydrofuran, acetonitrile or alcohols, in the presence of an inorganic base, such as an alkali metal hydroxide, for example sodium hydroxide, an alkali or alkaline-earth metal carbonate or bicarbonate, for example sodium carbonate, at room temperature for times ranging between about 1 and about 48 hours.

The resulting acid of formula (IV)

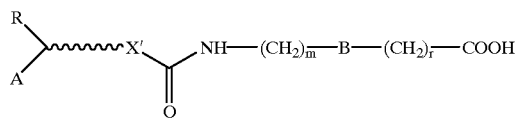

(IV)

wherein R, A, X', B, m and r are as defined above, is activated as the acyl chloride by treatment with thionyl chloride in chlorinated solvents or using thionyl chloride as the solvent, at a temperature ranging from room temperature to the solvent's reflux and for a time from about 1 to about 12 hours.

The acyl chloride is then reacted with an hydroxylamine hydrochloride in case a compound of formula (I) in which Y is hydroxy is desired, or with the suitable alkylenediamine in the other cases. The reaction takes place in a mixture of water and a water-miscible organic solvent such as tetrahydrofuran, acetonitrile, in the presence of an inorganic base as described in the above step, at room temperature for times ranging from about 1 to about 48 hours, to give the desired compound of formula (I).

Alternatively, acid (IV) is reacted with an hydroxylamine hydrochloride or an alkylenediamine in the presence of a condensing agent such as CDI, and of a tertiary amine such as triethylamine, in inert solvents such as acetonitrile, tetrahydrofuran, dioxane, chlorinated solvents, at room temperature for times ranging between about 1 and about 24 hours. The final compounds are purified according to the usual chromatography or crystallization techniques.

The compounds of formula (I) in which X is absent are prepared starting from the corresponding acid of formula (V)

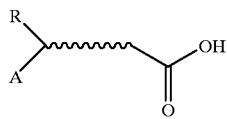

(V)

wherein R and A are as defined above, activated as the acyl chloride by treatment with thionyl chloride in chlorinated solvents or using thionyl chloride as the solvent, at a temperature ranging from room temperature to the solvent's reflux, for about 1–12 hours. The acyl chloride is reacted with the desired amino acid in a mixture of water and a water-miscible organic solvent, such as THF or acetonitrile, in the presence of a base such as an alkali metal hydroxide, for example sodium hydroxide, or an alkali or alkaline-earth metal carbonate or bicarbonate, such as sodium carbonate, at room temperature for about 1–12 hours.

The resulting compound of formula (VI)

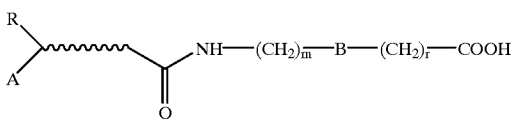

(VI)

wherein R, A, B, m and r are as defined above, is transformed into the desired compound of formula (I) following the procedures already described above 1.

In the following, examples of the preparation of some representative compounds of the invention are reported. $^1$H-NMR spectra were recorded in dimethylsulfoxide (DMSO) with a VARIAN GEMINI 200 spectrometer, if not otherwise indicated.

EXAMPLE 1

4-(5-Phenylpentanamido)benzohydroxamic acid

A. A solution of 5-phenylpentanoic acid (5 g, 28 mmoles) in chloroform (100 ml), was added with thionyl chloride (2,5 ml, 34 mmoles). The reaction mixture was refluxed for 4 hours, then evaporated to dryness. The residue was redissolved in chloroform and re-evaporated to dryness three times. The resulting 5-phenylpentanoyl chloride was dissolved in THF (50 ml) and the resulting solution was added slowly to a solution of 4-aminomethylbenzoic acid (3,8 g, 28 mmoles) in 1N sodium hydroxide (56 ml). The reaction mixture was stirred at room temperature for 3 hours, then THF was evaporated in the cold and the aqueous solution was acidified with HCl. The formed precipitate was filtered, redissolved in THF, dried over anhydrous calcium chloride and the solvent was evaporated off to give 6.7 g of 4-(5-phenylpentanamido)benzoic acid (81% yield); m.p.= 227–230° C.

$^1$H-NMR d 12.5 (s, 1 H, exchange with D₂O), 10.3 (s, 1H), 7.92 (d, 2H), 7.75 (d, 2H), 7.25 (m, 5H), 2.63 (t, 2H), 2.41 (t, 2H), 1.65 (m, 4H).

B. A solution of the compound obtained in A (6.7 g, 22 mmoles) in chloroform (100 ml) was added with thionyl chloride (3.3 ml, 45 mmoles) and 3 drops of pyridine. The reaction mixture was stirred at room temperature for 5 hours, then evaporated to dryness. The residue was redissolved in chloroform and re-evaporated to dryness three times. The resulting 4-(5-phenylpentanamido)benzoyl chloride was dissolved in THF (50 ml) and the resulting solution was added slowly to a solution of hydroxylamine hydrochloride (1.9 g, 27 mmoles) and sodium bicarbonate (1.9 g, 22 mmoles) in 1N sodium hydroxide (27 ml, 27 mmoles) and THF (25 ml). The reaction mixture was stirred at room temperature for 3 hours, then acidified with 1N HCl and THF was evaporated in the cold. The aqueous phase was extracted with ethyl acetate, and the combined organic phases were dried over anhydrous sodium sulfate and the solvent was evaporated off. The resulting crude was treated with warm ethyl ether and filtered to give 4.8 g of the title compound. (69% yield); m.p.=189–191° C.0

$^1$H-NMR d 11.12 (s, 1H), 10.13 (s, 1H), 8.97 (s, 1H), 7.691 (m, 4H), 7.33÷7.13 (m, 5H), 2.61 (m, 2H), 2.38 (m, 2H), 1.65÷1.58 (m, 4H).

EXAMPLE 2

4-[2,2-(Diphenyl)ethoxycarbamoylmethyl] benzohydroxamic acid

A. A mixture of 2,2-diphenylethanol (6 g, 30 mmoles), CDI (4.9 g, 30 mmoles) in THF (30 ml) was stirred at room temperature for 2 hours, then a solution of 4-aminomethylbenzoic acid (4.6 g, 30 mmoles) in 1N sodium hydroxide (30 ml) was added thereto. The reaction mixture was stirred at room temperature for 3 hours, then acidified with HCl, THF was evaporated in the cold, then the aqueous solution was extracted with ethyl acetate. The organic phase was dried over anhydrous sodium sulfate and the solvent was evaporated off. The resulting crude was treated with warm n-hexane and filtered to give 10 g of 4-[2,2-(diphenyl)ethoxycarbamoyl-methyl]benzoic acid (90% yield); m.p.=102–105° C.

$^1$H-NMR d 12.7 (s, 1H, exchange with $D_2O$), 7.91 (d, 2H), 7.78 (t, 1H), 7.50–7.20 (m, 12H), 4.61 (d, 2H), 4.38 (t, 1H), 4.23 (d, 2H).

B. A solution of the compound obtained in step A (4.5 g, 12 mmoles) in chloroform (50 ml), was added with thionyl chloride (1.3 ml, 18 mmoles) and 3 drops of pyridine. The reaction mixture was stirred at room temperature for 3 hours, then evaporated to dryness. The residue was redissolved in chloroform and re-evaporated to dryness three times. The resulting 4-[2,2(diphenyl)ethoxycarbamoylmethyl]-benzoyl chloride was dissolved in THF (50 ml) and the solution was added slowly to a solution of hydroxylamine hydrochloride (1.0 g, 14.4 mmoles) and sodium bicarbonate (1 g, 12 mmoles) in 1N sodium hydroxide (14.4 ml, 14.4 mmoles) and THF (20 ml). The reaction mixture was stirred at room temperature for 3 hours, then acidified with 1N HCl, and THF was evaporated in the cold. The aqueous phase was extracted with ethyl acetate, the combined organic phases were dried over anhydrous sodium sulfate and the solvent was evaporated off. The resulting crude was purified by column chromatography on silica gel (eluent: methylene chloride/methanol 15:1) and the resulting product was treated with warm ethyl ether and filtered thereby obtaining 1.5 g of the title compound (32% yield); m.p.=164–166° C.

$^1$H-NMR d 11.21 (s, 1H), 9.04 (s, 1H), 7.74 (t, 1H), 7.72 (m, 2H), 7.38÷7.20 (m, 12H), 4.60 (d, 2H), 4.38 (t, 1H), 4.20 (d, 2H).

EXAMPLE 3

4-[2-(Adamant-1-yl)-ethoxycarbamoyl] benzohydroxamic acid

A. A mixture of 2-(adamant-1-yl)ethanol (2.1 g, 12 mmoles), disuccinimidyl carbonate (3.3 g, 13 mmoles) and pyridine (0.86 ml, 10 mmoles) in acetonitrile (50 ml) was stirred at room temperature for 24 hours, then the solvent was evaporated off in the cold and the residue was dissolved in methylene chloride (100 ml). The solution was washed with water (50 ml), 1N HCl (50 ml) and water again (50 ml). The organic phase was dried over anhydrous sodium sulfate and the solvent was evaporated off to give 3 g (9 mmoles) of crude 2-(adamant-1-yl)ethyl-succinimidyl carbonate which was redissolved in THF (30 ml). The resulting solution was added to a solution of 4-aminobenzoic acid (1.3 g, 9 mmoles) and sodium carbonate (0.98 g, 9 mmoles) in water (30 ml), then stirred at room temperature overnight and acidified with HCl. THF was evaporated in the cold and the aqueous solution was extracted with ethyl acetate. The organic phase was dried over anhydrous sodium sulfate and the solvent was evaporated off. The resulting crude was treated with warm n-hexane and filtered, to yield 3.2 g of 4-[2-(adamant-1-yl)ethoxycarbamoyl]benzoic acid (77% yield); m.p.=197–200° C.

$^1$H-NMR d 12.6 (s, 1H, exchange with $D_2O$), 10.0 (s, 1H), 7.89 (d, 2H), 7.60 (d, 2H), 4.19 (t, 2H), 1.93 (m, 5H), 1.75–1.40 (m, 12H).

B. A solution of the compound obtained in step A (3 g, 8.7 mmoles) in chloroform (50 ml), was added with thionyl chloride (1.2 ml, 17.4 mmoles) and 3 drops of pyridine. The reaction mixture was refluxed for 5 hours, then evaporated to dryness. The residue was redissolved in chloroform and re-evaporated to dryness three times. The resulting 4-[2-(adamant-1-yl)ethoxycarbamoyl]benzoyl chloride was dissolved in THF (50 ml) and the solution was added slowly to a solution of hydroxylamine hydrochloride (0.7 g, 10.4 mmoles) and sodium bicarbonate (0,7 g, 8.7 mmoles) in 1N sodium hydroxide (10.4 ml, 10.4 mmoles) and THF (20 ml), then stirred at room temperature for 8 hours, acidified with 1N HCl, and THF was evaporated in the cold. The aqueous phase was extracted with ethyl acetate, the combined organic phases were dried over anhydrous sodium sulfate and the solvent was evaporated off. The resulting crude was treated with warm ethyl ether and filtered to give 1.5 g of the title compound (48% yield); m.p.=198–200° C.

$^1$H-NMR d 11.08 (s, 1H), 9.84 (s, 1H), 8.94 (s, 1H), 7.70 (m, 2H), 7.53 (m, 2H), 4.17 (m, 2H), 1.94 (m, 3H), 1.73÷1.37 (m, 14H).

EXAMPLE 4

4-[(Naphth-1-yl)methoxycarbamoyl] benzohydroxamic acid

A. Starting from naphth-1-yl-methanol (5 g, 31 mmoles), following the procedure described in Example 3A, 7 g of pure 4-[(naphth-1-yl)methoxy-carbamoyl]benzoic acid were obtained (81% yield).

$^1$H-NMR d 12.7 (s, 1H, exchange with $D_2O$), 10.2 (s, 1H), 8.18 (d, 1H), 7.97 (m, 4H), 7.61 (m, 6H), 5.69 (s, 2H).

B. Starting from the compound prepared in step A (6 g, 19 mmoles), following the procedure described in Example 3B, 1.86 g of the title compound were obtained (30% yield); m.p.=192–194° C.

$^1$H-NMR d 11.12 (s, 1H), 10.06 (s, 1H), 8.98 (s, 1H), 8.14 (m, 1H), 8.03÷7.96 (m, 2H), 7.76÷7.50 (m, 8H), 5.67 (s, 2H).

EXAMPLE 5

4-[(1,2,3,4-Tetrahydronaphth-2-yl) methoxycarbamoyl]-benzohydroxamic acid

A. Starting from (1,2,3,4-tetrahydronaphth-2-yl)methanol (4 g, 24 mmoles), following the procedure described in Example 3A, 5.2 g of pure 4-[(1,2,3,4-tetrahydronaphth-2-yl)methoxycarbamoyl]benzoic acid were obtained (67% yield); m.p.=203–206° C.

$^1$H-NMR d 12.6 (s, 1H, exchange with $D_2O$), 10.1 (s, 1H), 7.92 (d, 2H), 7.63 (d, 2H), 7.1 (m, 4H), 4.14 (d, 2H), 2.88 (m, 3H), 2.54 (m, 1H), 2.25–1.90 (m, 2H), 1.49 (m, 1H).

B. Starting from the compound of step A (5.2 g, 16 mmoles), following the procedure described in Example 3B, 4.1 g of the title compound were obtained (75% yield); m.p.=184–186° C.

$^1$H-NMR d 11.10 (s, 1H), 9.97 (s, 1H), 8.96 (s, 1H), 7.72 (m, 2H), 7.54 (m, 2H), 7.09 (s, 4H), 4.11 (d, 2H), 2.92÷2.75 (m, 3H), 2.61÷2.47 (m, 1H), 2.17÷1.93 (m, 2H), 1.56÷1,35 (m, 1H).

EXAMPLE 6

4-[(3-Phenylpropoxy)carbamoyl]benzohydroxamic acid

A. Starting from 3-phenylpropanol (5 g, 36 mmoles), following the procedure described in Example 3A, 7.7 g of pure 4-[(3-phenylpropoxy)carbamoyl]benzoic acid were obtained (71% yield); m.p.=171–173° C.

1H-NMR d 12.6 (s, 1H, exchange with $D_2O$), 10.1 (s, 1H), 7.90 (d, 2H), 7.61 (d, 2H), 7.28 (m, 5H), 4.13 (t, 2H), 2.72 (t, 2H), 1.98 (m, 2H).

B. Starting from the product of step A (7 g, 23 mmoles), following the procedure described in Example 3B, 5.8 g of the title compound were obtained (80% yield); m.p.=179–181° C.

$^1$H-NMR d 11.09 (s, 1H), 9.94 (s, 1H), 8.95 (s, 1H), 7.71 (m, 2H), 7.54 (m, 2H), 7.36÷7.15 (m, 5H), 4.10 (t, 2H), 2.70 (m, 2H), 1.95 (m, 2H).

EXAMPLE 7

4-[(Naphth-2-yl)methoxycarbamoyl]benzohydroxamic acid

A. Starting from naphth-2-yl-methanol (5 g, 31 mmoles), following the procedure described in Example 3A, 6.6 g of pure 4-[(naphth-2-yl)methoxycarbamoyl]benzoic acid were obtained (68% yield); m.p.=241–243° C.

$^1$H-NMR d 12.7 (s, 1H, exchange with $D_2O$), 10.2 (s, 1H), 7.95 (m, 6H), 7.60 (m, 5H), 5.39 (s, 2H).

B. Starting from the compound of step A (6 g, 18.6 mmoles), following the procedure described in Example 3B, 4.5 g of the title compound were obtained (72% yield); m.p.=220–222° C. $^1$H-NMR d 11.10 (s, 1H), 11.01 (s, 1H), 8.95 (s, 1H), 7.99÷7.90 (m, 4H), 7.73 (m, 2H), 7.61÷7.50 (m, 5H), 5.36 (s, 2H).

EXAMPLE 8

(E)-4- [(3-Phenyl-prop-2-enyl) carbamoyl]benzohydroxamic acid

A. 1.75 g (13 mmoles) of trans-cinnamol were dissolved in 130 ml of acetonitrile under argon atmosphere, then 5 g (19 mmoles) of N,N'-disuccinimidyl-carbonate were added heating until complete dissolution, then the mixture was cooled at 20° C. and added with pyridine (0.65 ml, 1 g, 12 mmoles). The reaction mixture was covered with aluminium and stirred at room temperature for 30 hours. The solvent was evaporated off in the cold, the residue was taken up into ethyl acetate and washed repeatedly with 0.1N HCl, finally with water. The solution was dried, then evaporated to dryness in the cold, to give a crude which was dissolved in 26 ml of dioxane and added to a solution of p-aminobenzoic acid (1.79 g, 13 mmoles) in 26 ml of water with 1.38 (13 mmoles) of sodium carbonate. The solution was stirred at room temperature for 60 hours, then added with THF and brine. The organic phase was separated and washed with 0.1N HCl (twice) and again with brine, then dried and !portata a secco stripped. The resulting crude was taken up into isopropyl ether and filtered, thereby obtaining 0.7 g of (E)-4-[(3-phenyl-prop-2-enyl)-carbamoyl]benzoic acid (18% yield); m.p.=176–178° C.

$^1$H-NMR d 12.70 (s, 1H, exchange with $D_2O$), 10.20 (s, 1H), 7.93 (d, 2H), 7.61 (d, 2H), 7.55÷7.25 (m, 5H), 6.78 (d, 1H), 6.46 (dt, 1H), 4.87 (d, 2H).

B. The compound of step A (0.7 g, 2.3 mmoles) was dissolved in 8 ml of anhydrous THF and added at 0° C. with CDI (0.46 g, 2.8 mmoles). The mixture was stirred at room temperature overnight, then hydroxylamine hydrochloride (0.2 g, 2.3 mmoles) was added thereto and stirring was continued at room temperature for a further 60 hours. The formed precipitate was filtered and suspended in 1N HCl, then stirred overnight. Upon filtration and drying under vacuum, 400 mg of the title compound were obtained (55.6% yield); m.p.=194–195° C.

$^1$H-NMR d 11.14 (s, 1H, exchange with $D_2O$), 10.07 (s, 1H), 8.97 (s, 1H, exchange with $D_2O$), 7.75 (d, 2H), 7.65÷7.25 (m, 7H), 6.79 (d, 1H), 6.48 (dt, 1H), 4.85 (d, 2H).

EXAMPLE 9

(Z)-4-[(3-Phenyl-prop-2-enyl)carbamoyl]benzohydroxamic acid

A. Starting from cis-cinnamol (2.82 g, 20 mmoles), following the procedure described in Example 8A, 2.4 g of (Z)-4-[(3-phenyl-prop-2-enyl)carbamoyl]-benzoic acid were obtained (40% yield).

$^1$H-NMR d 12.72 (s, 1H, exchange with $D_2O$), 10.20 (s, 1H), 7.92 (d, 2H), 7.60 (d, 2H), 7.55÷7.25 (m, 5H), 6.73 (d, 1H). 5.91 (dt, 1H), 4.96 (d, 2H).

B. Starting form the product of step A (0.7 g, 2.3 mmoles), following the procedure described in Example 8B, 400 mg of the title compound were obtained (55.6% yield); m.p.=169–170° C.

$^1$H-NMR d 11.13 (s, 1H, exchange with $D_2O$), 10.05 (s, 1H), 8.98 (s, 1H, exchange with $D_2O$), 7.74 (d, 2H), 7.55 (d, 2H), 7.50÷7.25 (m, 5H), 6.77 (d, 1H), 5.90 (dt, 1H), 4.94 (d, 2H).

EXAMPLE 10

4-[3.3-(Diphenyl)propoxycarbamoyl]benzohydroxamic acid

A. Starting from 3,3-diphenylpropanol (3 g, 14 mmoles), following the procedure described in Example 3A, 4.2 g of 4-[3,3(diphenyl)propoxycarbamoyl]benzoic acid were obtained (80% yield); m.p.=156–159° C.

$^1$H-NMR d 12.6 (s, 1H, exchange with $D_2O$), 10.1 (s, 1H), 7.90 (d, 2H), 7.60 (d, 2H), 7.40÷7.15 (m, 10H), 4.17 (t, 1H), 4.03 (t, 2H), 2.46 (m, 2H).

B. Starting from the compound obtained in step A (4.0 g, 10 mmoles), following the procedure described in Example 3B, 1 g of the title compound was obtained (26% yield), m.p.=196–197° C.

$^1$H-NMR d 11.08 (s, 1H), 9.93 (s, 1H), 8.93 (s, 1H), 7.70 (m, 2H), 7.54 (m, 2H), 7.39÷7.15 (m, 10H), 4.15 (t, 1H), 3.99 (t, 2H), 2.44 (q, 2H).

EXAMPLE 11

N-(2-Aminoethyl-4-[(fluoren-9-yl)methoxy-carbamoylmethyl]benzamide.HCl

A. A solution of 9-fluorenylmethyl chloroformate (5 g, 19 mmoles) in THF (50 ml) was added slowly to a solution of 4-aminomethyl benzoic acid (2.9 g, 19 mmoles). The reaction mixture was stirred at room temperature for 3 hours, then acidified with 1N HCl, and THF was evaporated in the cold. The aqueous phase was extracted with ethyl acetate, the combined organic phases were dried over anhydrous sodium sulfate and the solvent was evaporated off. The resulting crude was treated with warm ethyl ether and filtered to give 7 g of 4-[(fluoren-9-yl)methoxy-carbamoylmethyl]benzoic acid (98% yield); m.p.=232–235° C.

¹H-NMR d 12.7 (s, 1H, exchange with D$_2$O), 7.94 (m, 5H), 7.77 (d, 2H), 7.58÷7.30 (m, 6H), 4.42 (d, 2H), 4.30 (m, 3H).

B. A solution of the compound obtained in step A (3.7 g, 10 mmoles) in chloroform (100 ml) was added with thionyl chloride (1.46 ml, 20 mmoles), and the reaction mixture was refluxed for 2 hours, then evaporated to dryness. The residue was dissolved in chloroform and re-evaporated three times. The resulting 4-[(fluoren-9-yl)methoxy-carbamoylmethyl] benzoyl chloride was dissolved in THF (30 ml) and the solution was added slowly to a solution of 2-(t-butyloxyimino)ethylamine (1.6 g, 10 mmoles) and sodium bicarbonate (0.8 g, 10 mmoles) in water (20 ml) and THF (30 ml). The reaction mixture was stirred at room temperature for 12 hours, then THF was evaporated in the cold, the aqueous phase was acidified with 1N HCl and extracted with ethyl acetate. The organic phases were dried over anhydrous sodium sulfate and the solvent was evaporated off. The resulting crude was treated with warm ethyl ether and filtered to give 3.85 g of N-(2-t-butyloxycarbamoylmethyl)-4-[(fluoren-9-yl)methoxy carbamoylmethyl]benzamide (75% yield); m.p.=167–169° C.

¹H-NMR d 8.45 (t, 1H), 7.94÷7.70 (m, 7H), 7.54÷7.25 (m, 6H), 6.96 (t, 1H), 4.42 (d, 2H), 4.27 (m, 3H), 3.32 (q, 2H), 3.13 (q, 2H), 1.41 (s, 9H).

C. The product of step B (3.6 g, 7 mmoles) was added in small portions to trifluoroacetic acid (25 ml) at 0° C. The mixture was stirred at room temperature for 4 hours, then the acid was evaporated and the residue was taken up into warm ethyl ether and filtered to give a product which was dissolved in THF and methanol, and a HCl ether solution was added thereto. The solvents were evaporated off and the procedure was repeated 4 times. The crude was taken up into some water at 0° C. and filtered to give 2 g of the title compound (65% yield); m.p.=182–184° C.

¹H-NMR d 8.79 (t, 1H), 8.17 (s, 3H), 7.96÷7.86 (m, 5H), 7.72 (m, 2H), 7.48÷7.29 (m, 6H), 4.38 (m, 2H), 4.25 (m, 3H), 3.55 (q, 2H), 3.00 (t, 2H).

EXAMPLE 12

4-[6-(Diethylaminomethyl)naphth-2-ylmethyloxycarbamoyl]-benzohydroxamic acid hydrochloride A. 1-(3-Dimethylaminopropyl)-3-ethylcarbodiimide hydrochloride (EDCI) (22.2 g, 115 mmol) was added to a solution of 2,6-naphthalenedicarboxylic acid (25 g, 115 mmol) and hydroxybenzotriazole (15.6 g, 115 mmol) in dimethylformamide (1800 ml) and the mixture was stirred at room temperature for 2 hours. Diethyl amine (34.3 ml, 345 mmol) was added and the solution was stirred overnight at room temperature. The solvent was then evaporated under reduced pressure and the crude was treated with 1N HCl (500 ml) and ethyl acetate (500 ml), insoluble compounds were filtered off and the phases were separated. The organic phase was extracted with 5% sodium carbonate (3×200 ml) and the combined aqueous solutions were acidified with concentrated HCl and extracted with ethyl acetate (3×200 ml). The organic solution was then washed with 1N HCl (6×100 ml), dried over anhydrous sodium sulphate and the solvent was removed under reduced pressure yielding 18.5 g (Yield 60%) of pure 6-(diethylaminocarbonyl)-2-naphthalenecarboxylic acid; m.p.=122–124° C.

¹H-NMR d 8.67 (s, 1H), 8.25–8.00 (m, 4H), 7.56 (d, 1H), 3.60–3.20 (m, 4H), 1.30–1.00 (m, 6H).

B. A solution of 6-(diethylaminocarbonyl)-2- naphthalenecarboxylic acid (18 g, 66 mmol) in THF (200 ml) was slowly added to a refluxing suspension of lithium aluminium hydride (7.5 g, 199 mmol) in THF (500 ml). The mixture was refluxed for an hour, then cooled at room temperature and treated with a mixture of THF (25 ml) and water (3.5 ml), with 20% sodium hydroxide (8.5 ml) and finally with water (33 ml). The white solid was filtered off and the solvent was removed under reduced pressure. Crude was dissolved in diethyl ether (200 ml) and extracted with 1N HCl (3×100 ml). The aqueous solution was treated with 32% sodium hydroxide and extracted with diethyl ether (3×100 ml). The organic solution was dried over anhydrous sodium sulphate and the solvent was removed under reduced pressure yielding 12.7 g (79% yield) of pure 6-(diethylaminomethyl)-2-naphthalenemethanol as thick oil.

¹H-NMR d 7.90–7.74 (m, 4H), 7.49 (m, 2H), 5.32 (t, 1H, exchange with D$_2$O), 4.68 (d, 2H), 3.69 (s, 2H), 2.52 (q, 4H), 1.01 (t, 6H).

C. A solution of 6-(diethylaminomethyl)-2-naphthalenemethanol (12.5 g, 51 mmol) and N,N'-disuccinimidyl carbonate (13.2 g, 51 mmol) in acetonitrile (250 ml) was stirred at room temperature for 3 hours, then the solvent was removed and the crude was dissolved in THF (110 ml). This solution was added to a solution of 4-amino benzoic acid (7.1 g, 51 mmol) and sodium carbonate (5.5 g, 51 mmol) in water (200 ml) and THF (100 ml). The mixture was stirred overnight at room temperature, then THF was removed under reduced pressure and the solution was treated with 1N HCl (102 ml, 102 mmol). The precipitate was filtered, dried under reduced pressure, tritured in diethyl ether and filtered yielding 13.2 g (yield 64%) of pure 4-[6-(diethylaminomethyl)naphth-2-ylmethyloxycarbamoyl]-benzoic acid; m.p.=201–205° C. (dec.)

¹H-NMR d 10.26 (s, 1H), 8.13 (s, 1H), 8.05–7.75 (m, 6H), 7.63 (m, 3H), 5.40 (s, 2H), 4.32 (s, 2H), 2.98 (q, 4H), 1.24 (t, 6H).

D. A solution of 4-[6-(diethylaminomethyl)naphth-2-ylmethyloxycarbamoyl]benzoic acid (13.1 g, 32 mmol) and thionyl chloride (7 ml, 96 mmol) in chloroform (300 ml) was refluxed for 4 hours, then the solvent and thionyl chloride were evaporated. Crude was dissolved in chloroform (100 ml) and evaporated to dryness three times. Crude was added as solid to a solution of hydroxylamine hydrochloride (2.7 g, 39 mmol) and sodium bicarbonate (5.4 g, 64 mmol) and 1N sodium hydroxide (39 ml, 39 mmol) in water (150 ml) and THF (50 ml). The mixture was stirred overnight at room temperature, then THF was removed under reduced pressure and the aqueous phase was extracted with ethyl acetate (3×100 ml). The combined organic phases were dried over anhydrous sodium sulphate and the solvent was removed under reduced pressure. Crude was dissolved in THF and treated with a 1.5 N etheric solution of HCl. The solid product was filtered and dried yielding 6 g (yield 41%) of pure 4-[6-(diethylaminomethyl)naphth-2-ylmethyloxycarbamoyl]benzohydroxamic acid hydrochloride as white solid; m.p.=162–165° C., (dec.)

¹H-NMR d 11.24 (s, 1H, exchange with D$_2$O), 10.88 (s, 1H, exchange with D$_2$O), 10.16 (s, 1H), 8.98 (bs, 1H, exchange with D$_2$O), 8.21 (s, 1H), 8.10–7.97 (m, 3H), 7.89 (d, 1H), 7.80–7.55 (m, 5H), 5.39 (s, 2H), 4.48 (d, 2H), 3.09 (m, 4H), 1.30 (t, 6H).

EXAMPLE 13

4-[6-(Dipropylaminomethyl)naphth-2-ylmethyloxycarbamoyl]benzohydroxamic acid hydrochloride Starting from 2,6-naphthalenedicarboxylic acid (5 g) and dipropyl amine (9.6 ml) and following the same procedure described in Example 12, 1 g of pure 4-[6-(dipropylaminomethyl)naphth-2-ylmethyloxycarbamoyl] benzohydroxamic acid hydrochloride was obtained as white solid; m.p.=140–142° C. (dec.)

$^1$H-NMR d 11.15 (s, 1H, exchange with D$_2$O), 10.95 (s, 1H, exchange with D$_2$O), 10.16 (s, 1H), 8.20 (s, 1H), 8.10–7.97 (m, 3H), 7.89 (d, 1H), 7.80–7.55 (m, 5H), 5.40 (s, 2H), 4.50 (d, 2H), 2.98 (m, 4H), 1.79 (m, 4H), 0.88 (t, 6H).

EXAMPLE 14

4-[6-(Dibutylaminomethyl)naphth-2-ylmethyloxycarbamoyl]benzohydroxamic acid hydrochloride Starting from 2,6-naphthalenedicarboxylic acid (5 g) and dibutyl amine (11.8 ml) and following the same procedure described in Example 12, 1.2 g of pure 4-[6-(dibutylaminomethyl)naphth-2-ylmethyloxycarbamoyl] benzohydroxamic acid hydrochloride were obtained as white solid; m.p.=137–141° C. (dec.) $^1$H-NMR d 11.19 (s, 1H, exchange with D$_2$O), 10.91 (s, 1H, exchange with D$_2$O), 10.16 (s, 1H), 8.96 (bs, 1H, exchange with D$_2$O), 8.21 (s, 1H), 8.10–7.98 (m, 3H), 7.87 (d, 1H), 7.80–7.55 (m, 5H), 5.38 (s, 2H), 4.52 (d, 2H), 3.02 (m, 4H), 1.77 (m, 4H), 1.30 (m, 4H), 0.89 (t, 6H).

EXAMPLE 15

4-[4-(Diethylaminomethyl)naphth-1-ylmethyloxycarbamoyl]-benzohydroxamic acid hydrochloride Starting from 1,4-naphthalenedicarboxylic acid (5 g) and diethyl amine (7.3 ml) and following the same procedure described in the example 12, 1.1 g of pure 4-[4-(diethylaminomethyl)naphth-1-ylmethyloxycarbamoyl]-benzohydroxamic acid hydrochloride were obtained as white solid; m.p.=162–165° C. (dec.)

$^1$H-NMR d 11.24 (s, 1H, exchange with D$_2$O), 10.48 (s, 1H, exchange with D$_2$O), 10.13 (s, 1H), 8.43 (m, 1H), 8.26 (m, 1H), 8.04 (d, 1H), 7.82–7.70 (m, 5H), 7.58 (d, 2H), 5.73 (s, 2H), 4.84 (d, 2H), 3.17 (m, 4H), 1.32 (t, 6H).

EXAMPLE 16

4-[6-(Diethylaminomethyl)naphth-2-ylmethylaminocarbamoyl]benzohydroxamic acid hydrochloride.

A. A solution of 6-(diethylaminocarbonyl)-2-naphthalenecarboxylic acid (prepared as reported in example 12 A) (14 g, 52 mmol) and thionyl chloride (3.8 ml, 52 mmol) in chloroform (200 ml) was refluxed for 3 hours, then the solvent and thionyl chloride were evaporated. Crude was dissolved in chloroform (100 ml) and evaporated to dryness three times. Crude was dissolved in THF (50 ml) and added at 0° C. to a solution of 32% ammonium hydroxide (10 ml) in water (50 ml) and THF (50 ml). The mixture was stirred overnight at room temperature, then THF was removed under reduced pressure and the solid was filtered and dried yielding 11.6 g (yield 81%) of 6-(diethylaminocarbonyl)-2-naphthalenecarboxamide which was used for the next step without further purification.

B. A solution of 6-(diethylaminocarbonyl)-2-naphthalenecarboxamide (11.6 g, 42 mmol) in THF (100 ml) was slowly added to a refluxing suspension of lithium aluminium hydride (4.9 g, 128 mmol) in THF (100 ml). The mixture was refluxed for 2 hours, then cooled at room temperature and treated with a mixture of THF (16 ml) and water (2.2 ml), with 20% sodium hydroxide (5.5 ml) and finally with water (22 ml). The white solid was filtered off and the solvent was removed under reduced pressure. Crude was purified by chromatography on silica gel (eluent chloroform-methanol-ammonium hydroxide 15:1:0.1) yielding 8.1 g (Yield 80%) of pure 6-(diethylaminomethyl)-2-naphthylmethylamine as waxy solid.

$^1$H-NMR d 7.78 (m, 4H), 7.49 (m, 2H), 3.89 (s, 2H), 3.67 (s, 2H), 2.50 (q, 4H), 1.00 (t, 6H).

C. A solution of 6-(diethylaminomethyl)-2-naphthylmethylamine (6 g, 24 mmol) and N,N'-disuccinimidyl carbonate (6.3 g, 24 mmol) in acetonitrile (200 ml) was stirred at room temperature for 3 hours, then this solution was added to a solution of 4-aminobenzoic acid (3.4 g, 24 mmol) and sodium carbonate (2.6 g, 24 mmol) in water (100 ml) and THF (100 ml). The mixture was stirred at room temperature for 48 hours, then 1N HCl (48 ml, 48 mmol) was added and the solvents were removed under reduced pressure. The crude product was purified by chromatography on silica gel (eluent chloroform-methanol-ammonium hydroxide 7:3:0.5) yielding 3.5 g (yield 36%) of pure 4-[6-(diethylaminomethyl)naphth-2-ylmethylaminocarbamoyl] benzoic acid. m.p.=179–183° C. (dec.)

$^1$H-NMR d 9.58 (s, 1H), 7.95–7.78 (m, 6H), 7.65–7.45 (m, 4H), 7.29 (t, 1H), 4.51 (d, 2H), 3.81 (s, 2H), 2.62 (q, 4H), 1.07 (t, 6H)

D. A solution of 4-[6-(diethylaminomethyl)naphth-2-ylmethylaminocarbamoyl]benzoic acid (3.1 g, 7.6 mmol) and thionyl chloride (1.1 ml, 15.2 mmol) in dimethylformamide (30 ml) was stirred overnight at room temperature, then the suspension was diluted with diethyl ether and the solid was filtered and dried yielding 3.2 g of crude 4-[6-(diethylaminomethyl)naphth-2-ylmethylaminocarbamoyl] benzoyl chloride. This compound was added as solid to a solution of hydroxylamine hydrochloride (0.6 g, 8.5 mmol) and sodium bicarbonate (1.2 g, 14 mmol) and 1N sodium hydroxide (8.5 ml, 8.5 mmol) in water (30 ml) and THF (40 ml). The mixture was stirred at room temperature for 2 hours, then the mixture was saturated with sodium chloride and the organic phase was separated and the aqueous phase was extracted with THF. The combined organic phases were dried foyer anhydrous sodium sulphate and the solvent was removed under reduced pressure. Crude was dissolved in hot THF (150 ml) and the insoluble material was filtered off. The solution was cooled at room temperature and treated with 1.5 N etheric solution of HCl. The solid product was filtered and dried yielding 1.2 g (yield 38%) of pure 4-[6-(diethylaminomethyl)naphth-2-ylmethylaminocarbamoyl]-benzohydroxamic acid hydrochloride as white solid; m.p.= 167–168° C. (dec.)

$^1$H-NMR d 11.07 (s, 1H, exchange with D$_2$O), 10.49 (bs, 1H, exchange with D$_2$O), 9.49 (s, 1H), 8.93 (s, 1H, exchange with D$_2$O), 8.15 (s, 1H), 8.05–7.87 (m, 3H), 7.81 (d, 1H), 7.72 (d, 2H), 7.65–7.50 (m, 3H), 7.27 (t, 1H), 4.54 (d, 2H), 4.48 (s, 2H), 3.11 (m, 4H), 1.30 (t, 6H)

EXAMPLE 17

4-[N-isopropyl-1,2,3,4-tetrahydroisoquinol-3-yl) methyloxycarbamoylmethyl]benzohydroxamic acid hydrochloride A. A solution of 1,2,3,4-tetrahydro-3-isoquinolinecarboxylic acid (9 g, 42 mmol), 2-bromopropane (8 ml, 84 mmol) and 1N NaOH (168 mmol) in ethanol (170 ml) was refluxed for 5 hours, then 2-bromopropane (8 ml, 84 mmol)

and 1N NaOH (168 ml, 168 mmol) were added and the mixture was refluxed for 5 hours. Ethanol was removed and the aqueous solution was treated with 6N hydrochloric acid to pH=7. Unreacted starting material was recovered by filtration and the solvent was removed under reduced pressure. The crude was dissolved in ethanol, the inorganics salts were filtered off and the organic solution was evaporated under reduced pressure. This procedure was repeated three times yielding 8.1 g (yield 87%) of pure N-isopropyl-1,2, 3,4-tetrahydro-3-isoquinolinecarboxylic acid which was used for the next step without further purification.

$^1$H-NMR δ7.13 (m, 4H), 4.16 (d, 1H), 3.89 (d, 1H), 3.58 (t, 1H), 3.43 (m, 1H), 3.13 (dd, 1H), 2.94 (dd, 1H), 1.19 (d, 3H), 1.11 (d, 3H).

B. A sospension of N-isopropyl-1,2,3,4-tetrahydro-3-isoquinolinecarboxylic acid (8.0 g, 36 mmol) in tetrahydrofuran (100 ml) was slowly added to a refluxing suspension of lithium aluminum hydride (2.1 g, 54 mmol) in tetrahydrofuran (100 ml). The mixture was refluxed for two hours, then cooled at room temperature and treated with a mixture of tetrahydrofuran (7 ml) and water (0.9 ml), with 20% sodium hydroxide (2.3 ml) and finally with water (9.2 ml). The white solid was filtered off and the solvent was removed under reduced pressure yielding 5.0 g (yield 68%) of pure N-isopropyl-1,2,3,4-tetrahydroisoquinol-3-ylmethanol as thick oil. $^1$H-NMR δ7.12 (m, 4H), 4.54 (bs, 1H, exchange with $D_2O$), 3.68 (s, 2H), 3.55–3.35 (m, 2H), 3.20–2.90 (m, 2H), 2.79 (d, 2H), 1.10 (d, 3H), 1.01 (d, 3H).

C. A solution of N-isopropyl-1,2,3,4-tetrahydroisoquinolin-3-ylmethanol (4.6 g, 22.4 mmol) and 1,1'-carbonyldiimidazole (3.63 g, 22.4 mmol) in tetrahydrofuran (50 ml) was stirred at room temperature for 3 hours. Then this solution was added to a solution of 4-aminomethylbenzoic acid (3.38 g, 22.4 mmol) and 1N sodium hydroxide (22.4 ml, 22.4 mmol) in water (20 ml). The solution was stirred overnight at room temperature, then 1N hydrochloric acid (22.4 ml, 22.4 mmol) was added and the solvents removed under reduced pressure. The crude product was purified by chromatography on silica gel (eluent chloroform-methanol-ammonium hydroxide 8:2:0.5) yielding 3.1 (yield 35%) of pure 4-[(N-isopropyl-1,2,3,4-tetrahydroisoquinol-3-yl)-methyloxycarbamoyl]benzoic acid as white solid. m.p.=93–95° C. (dec.).

$^1$H-NMR δ7.92 (d, 2H), 7.86 (t, 1H), 7.36 (t, 2H), 7.14 (m, 4H), 4.26 (d, 2H), 4.07 (dd, 1H), 3.73 (s, 2H), 3.68 (dd, 1H), 3.25 (m, 1H), 3.02 (m, 1H), 2.89 (dd, 1H), 2.72 (dd, 1H), 1.10 (d, 3H), 1.04 (d, 3H).

D. A solution of 4-[(N-isopropyl-1,2,3,4-tetrahydroisoquinol-3-yl)methyloxycarbamoyl]benzoic acid (3.0 g, 7.8 mmol) and thionyl chloride (1.7 ml, 23 mmol) in chloroform (100 ml) was refluxed for 3 hours, then the solvent and thionyl chloride were evaporated. Crude was dissolved in chloroform (100 ml) and evaporated to dryness three times. Crude was dissolved in tetrahydrofuran (50 ml) and added to a solution of hydroxylamine hydrochloride (0.65 g, 9.4 mmol) and sodium bicarbonate (1.3 g, 15.7 mmol) and 1N sodium hydroxide (9.4 ml, 9.4 mmol) in water (30 ml) and tetrahydrofuran (20 ml). The mixture was at room temperature for an hour, then tetrahydrofuran was removed under reduced pressure and the aqueous phase was extracted with ethyl acetate (3×100 ml). The combined organic phases were dried over anhydrous sodium sulphate and the solvent was removed under reduced pressure. Crude was dissolved in tetrahydrofuran and treated with a 1.5 N etheric solution of hydrochloric acid. The solid product was filtered and dried yielding 2.1 g (yield 62%) of pure 4-[(N-isopropyl-1,2,3,4-tetrahydroisoquinol-3-yl) methyloxycarbamoyl]benzohydroxamic acid hydrochloride as white solid. m.p.=154–157° C. (dec.).

$^1$H-NMR δ11.24 (s, 1H), 10.75 (s, 1H), 9.07 (bs, 1H), 8.01 (t, 1H), 7.70 (d, 2H), 7.34 (d, 2H), 7.32 (m, 4H), 4.38 (d, 2H), 4.26 (m, 4H), 4.02 (m, 1H), 3.78 (m, 1H), 3.15 (d, 2H), 1.42 (d, 3H), 1.30 (d, 3H).

The following compounds can be prepared analogously to what reported above:

4-[(4-dimethylaminomethyl-naphth-2-yl)methoxycarbamoyl]benzohydroxamic acid

4-[(4-diethylaminoethyl-naphth-2-yl)methoxycarbamoyl]benzohydroxamic acid

4-[(4-dimethylaminoethyl-naphth-2-yl)methoxycarbamoyl]benzohydroxamic acid

4-[(6-dimethylaminomethyl-naphth-2-yl)methoxycarbamoyl]benzohydroxamic acid

4-[(6-di-iso-propylaminomethyl-naphth-2-yl)methoxycarbamoyl]benzohydroxamic acid 4-[(4-dimethylaminomethyl-naphth-2-yl)methoxycarbamoyl]methylbenzohydroxamic acid 4-[(4-dimethylaminomethyl-naphth-2-yl)ethoxycarbamoyl]benzohydroxamic acid 4-[(5,6,7,8-tetrahydronaphth-2-yl)methoxycarbamoyl]benzohydroxamic acid 4-[N-(1,2,3,4-tetrahydronaphth-2-yl)glycinamido]-benzohydroxamic acid 4-[(4-diethylaminomethyl-naphth-2-yl)ethoxycarbamoyl]benzohydroxamic acid 4-[(6-dimethylaminomethyl-naphth-2-yl)ethoxycarbamoyl]benzohydroxamic acid 4-[(6-diethylaminomethyl-naphth-2-yl)ethoxycarbamoyl]benzohydroxamic acid 4-[(1,2,3,4-tetrahydronaphth-2-yl)methoxycarbanmoyl]benzohydroxamic acid 4-[(4-dimethylaminomethyl-naphth-1-yl)methoxycarbamoyl]benzohydroxamic acid 4-[(4-dimethylaminoethyl-naphth-1-yl)methoxycarbamoyl]benzohydroxamic acid 4-[(5-dimethylaminomethyl-naphth-1-yl)methoxycarbamoyl]benzohydroxamic acid 4-[(5-diethylaminomethyl-naphth-1-yl)methoxycarbamoyl]benzohydroxamic acid 4-[(5-di-n-propylaminomethyl-naphth-1-yl)methoxycarbamoyl]benzohydroxamic acid 4-[(5-di-iso-propylaminomethyl-naphth-1-yl)methoxycarbamoyl]benzohydroxamic acid 4-[(5-di-n-butylaminomethyl-naphth-1-yl)methoxycarbamoyl]benzohydroxamic acid 4-[(6-dimethylaminomethyl-naphth-1-yl)methoxycarbamoyl]benzohydroxamic acid 4-[(6-diethylaminomethyl-naphth-1-yl)methoxycarbamoyl]benzohydroxamic acid 4-[(6-di-n-propylaminomethyl-naphth-1-yl)methoxycarbamoyl]benzohydroxamic acid 4-[(6-di-iso-propylaminomethyl-naphth-1-yl)methoxycarbamoyl]benzohydroxamic acid 4-[(6-di-n-butylaminomethyl-naphth-1-yl)methoxycarbamoyl]benzohydroxamic acid 4-[(4-dimethylaminomethyl-naphth-1-yl)methoxycarbamoyl]methyl-benzohydroxamic acid 4-[(4-dimethylaminomethyl-naphth-1-yl)ethoxycarbamoyl]benzohydroxamic acid 4-[(4-diethylaminomethyl-naphth-1-yl)ethoxycarbamoyl]benzohydroxamic acid 4-[(5-dimethylaminomethyl-naphth-1-yl)ethoxycarbamoyl]benzohydroxamic acid 4-[(5-diethylaminomethyl-naphth-1-yl)ethoxycarbamoyl] benzohydroxamic acid
4-[(6-dimethylaminomethyl-naphth-1-yl)ethoxycarbamoyl] benzohydroxamic acid
4-[(6-diethylaminomethyl-naphth-1-yl)ethoxycarbamoyl] benzohydroxamic acid
4-[N-(naphth-1-yl-methyl)glycinamido]benzohydroxamic acid
4-[N-(naphth-2-yl-methyl)glycinamido]benzohydroxamic acid
4-[(N-methyl-1,2,3,4-tetrahydroisoquinol-5-yl)methoxycarbamoyl]benzohydroxamic acid
4-[(N-ethyl-1,2,3,4-tetrahydroisoquinol-5-yl)methoxycarbamoyl]benzohydroxamic acid
4-[(isoquinol-5-yl)methoxycarbamoyl]benzohydroxamic acid
4-[(N-methyl-1,2,3,4-tetrahydroisoquinol-6-yl)methoxycarbamoly]benzohydroxamic acid
4-[(N-ethyl-1,2,3,4-tetrahydroisoquinol-6-yl)methoxycarbamoyl]benzohydroxamic acid
4-[(isoquinol-6-yl)methoxycarbamoyl]benzohydroxamic acid
4-[(N-methyl-1,2,3,4-tetrahydroisoquinol-1-yl)methoxycarbamoyl]benzohydroxamic acid
4-[(N-ethyl-1,2,3,4-tetrahydroisoquinol-1-yl)methoxycarbamoyl]benzohydroxamic acid
4-[(isoquinol-1-yl)methoxycarbamoyl]benzohydroxamic acid
4-[(N-methyl-1,2,3,4-tetrahydroisoquinol-3-yl)methoxycarbamoyl]benzohydroxamic acid
4-[(N-ethyl-1,2,3,4-tetrahydroisoquinol-3-yl)methoxycarbamoyl]benzohydroxamic acid
4-[(isoquinol-3-yl)methoxycarbamoyl]benzohydroxamic acid
4-[(N-methyl-1,2,3,4-tetrahydroisoquinol-4-yl)methoxycarbamoyl]benzohydroxamic acid
4-[(N-ethyl-1,2,3,4-tetrahydroisoquinol-4-yl)methoxycarbamoyl]benzohydroxamic acid
4-[(isoquinol-4-yl)methoxycarbamoyl]benzohydroxamic acid
4-[3-(1,2,3,4-tetrahydroisoquinol-2-yl)propionamido]benzohydroxamic acid
4-[(benzothiophen-4-yl)methoxycarbamoyl]benzohydroxamic acid
4-[(benzothiophen-5-yl)methoxycarbamoyl]benzohydroxamic acid
4-[(benzofuran-4-yl)methoxycarbamoyl]benzohydroxamic acid
4-[(benzofuran-5-yl)methoxycarbamoyl]benzohydroxamic acid
4-[4-(diethylaminopropyl)naphth-1-ylmethyloxycarbamoyl]benzohydroxamic acid hydrochloride
4-[3-(diethylaminomethyl)naphth-1-ylmethyloxycarbamoyl]benzohydroxamic acid hydrochloride
4-[3-(diethylaminoethyl)naphth-1-ylmethyloxycarbamoyl] benzohydroxamic acid hydrochloride
4-[3-(diethylaminopropyl)naphth-1-ylmethyloxycarbamoyl]benzohydroxamic acid hydrochloride
4-[4-(diethylaminopropyl)naphth-1-ylmethylaminocarbamoyl]benzohydroxamic acid hydrochloride
4-[3-(diethylaminomethyl)naphth-1-ylmethylaminocarbamoyl]benzohydroxamic acid hydrochloride
4-[3-(diethylaminoethyl)naphth-1-ylmethylaminocarbamoyl]benzohydroxamic acid hydrochloride
4-[3-(diethylaminopropyl)naphth-1-ylmethylaminocarbamoyl]benzohydroxamic acid hydrochloride
4-[6-(dipropylaminomethyl)naphth-2-ylmethylaminocarbamoyl]benzohydroxamic acid hydrochloride
4-[6-(dibutylaminomethyl)naphth-2-ylmethylaminocarbamoyl]benzohydroxamic acid hydrochloride
4-[4-(diethylaminomethyl)naphth-1-ylmethylaminocarbamoyl]benzohydroxamic acid hydrochloride
4-[4-(dipropylaminomethyl)naphth-1-ylmethylaminocarbamoyl]benzohydroxamic acid hydrochloride
4-[4-(diethylaminoethyl)naphth-1-ylmethylaminocarbamoyl]benzohydroxamic acid hydrochloride.

Pharmacological activity

The anti-inflammatory and immunosuppressive activities of the compounds of the invention were tested both in vitro and in vivo.

1. In vitro cytokines production test

The compounds of the invention were tested by in particular on the production of human IL-1β. Mononuclear cells (PBMC) were prepared from peripheral blood ("buffy coat") from healthy donors, by centrifugation over density gradient Ficoll-Hypaque (Biochrom KG, Berlin, Germany). The cells ($2,5 \times 10^6$ for ml) were cultured at 37° C. under humid atmosphere containing 5% $CO_2$ in 96-wells plates (Nunc) at a final volume of 200 µl. The culture medium was RPMI 1640 N-acetyl-L-alanyl-L-glutamine with low endo-toxin content ("low endotoxin"; Biochrom KG), added with 1% of boyine foetal serum (Hyclone Laboratories Inc., Logan, Utah), 100 UI/ml of penicillin and 100 µg/ml of streptomycin. The production of cytokines was induced by stimulating the cells with 10 ng/ ml of LPS (lipopolysaccharide) from E. coli serotype 055:B5 (Sigma Chemical Co., St. Louis. Mo.). The cells were pretreated with the compounds of the intention dissolved in DMSO (final concentration: 0.05% yield) for 60 minutes. The compounds and LPS were present during the whole 20 hours of culture. As the negative control, not-stimulated cells were used. At the end of the test, supernatants were collected and the IL-1β production was tested by a specific ELISA assay ("sandwich-type antigen capture", R & D System, Minneapolis, Minn.; all of the tests were carried out in duplicate). A goat polyclonal serum specific for human IL-1β was used, purified by affinity, to cover the 96-wells microtitration plates (Nunc). After washing, the wells were incubated for 2 hours with 3% of boyine serum albumine (BSA) in buffered saline. Recombinant human IL-1β was used to obtain a standard curve for each test and the supernatant samples were diluted to 1/20 and 1/80 with PBS+0.1% of BSA. The plates were then incubated at 4° C. overnight. After washing, the secondary antibody was added, i.e. an anti- human IL-1β murine monoclonal antibody. After incubation and washing, a goat anti-murine Ig-G polyclonal antibody peroxidase-conjugated (Zymed) was added, then the chromogenic substrate tetramethylbenzidine dichloride (Sigma). The reaction was stopped with 4N $H_2SO_4$ and the absorbance at 450 nm was measured with an automatic spectrophotometer (Perkin-Elmer). The inhibitory activity of the compounds of the intention was expressed as IC50, i.e. the product concentration inhibiting by 50% the IL-1β production compared with a control culture.

TABLE 1

| Compound | IC$_{50}$ (nM) |
|---|---|
| Example 1 | 305 |
| Example 2 | 163 |
| Example 3 | 531 |
| Example 4 | 28 |
| Example 5 | 137 |
| Example 6 | 43 |
| Example 7 | 12 |
| Example 8 | 29 |
| Example 9 | 72 |
| Example 10 | 101 |
| Example 12 | 96 |
| Example 13 | 166 |
| Example 14 | 382 |
| Example 15 | 14 |
| Example 16 | 10 |
| Example 17 | 21 |
| Dexamethasone | 575 |

2. In vivo LPS-induced TNFα production Male BALB/c mice (18–20 g) were obtained from Harlan-Nossan (Correzzana, Italy); Lipopolysaccharide (LPS) from *S. enteritidis* (code L-6011) was from Sigma (St. Louis, Mo.); Dexamethasone (Soldesam) from Laboratorio Farmacologico Milanese (Caronno P., Italy).

Mice were treated i.p. with LPS (*S. enteritidis*, 7.5 mg/kg). Dexamethasone was administered i.p. 30 min. before LPS. Compounds were administered orally 90 min. before LPS. Two hours after LPS administration the anaesthetized animals were sacrificed, blood was collected by cardiac puncture and allowed to coagulate. Serum TNFα was measured by ELISA with "mouse Reagent Sets" (Genzyme, Cambridge, Mass.) according to the manufacturer's instructions and using mouse recombinant TNFα as standard.

TABLE 2

Effect of compound of example 12 on LPS-induced serum TNFα production.

| Treatment | TNFα (pg/ml) | Inhibition (%) |
|---|---|---|
| Saline (Control) | <0.1 LPS | |
| LPS | 1140 | |
| compound 12 (0.5 mg/kg) | 514 | 55.0 |
| compound 12 (5.0 ng/kg) | 407 | 64.3 |
| Dex (30 mg/kg) | 112 | 90.2 |

The obtained results evidence that the tested compounds are effective in inhibiting the production of both IL-1β and TNFα, being as or more active than dexamethasone, a control compound and well known antiinflammatory agent.

The present invention further relates to the use of the compounds of formula (I) as anti-inflammatory and immunosuppressive agents, as well as all of the industrially applicable aspects related thereto, including the incorporation thereof in pharmaceutical compositions. Examples of such pharmaceutical compositions are tablets, sugar-coated pills, creams, ointments and vials, the latter suitable for both the oral and intramuscular or intravenous administrations. They contain the active ingredient alone or in admixture with the conventional pharmaceutically acceptable carriers and excipients.

The dosages of the active ingredient can vary within wide limits, depending on the type of compound used, which may be administered one or more times daily, according to the therapeutical requirements.

We claim:

1. A compound of formula (I)

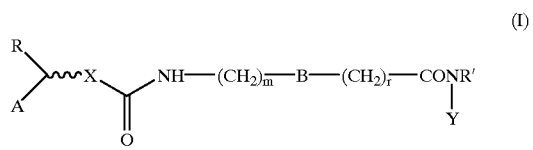

wherein R' is hydrogen;

A is adamantyl or a mono-, bi-, or tricyclic residue optionally partially or totally unsaturated, which can contain one or more heteroatoms selected from the group consisting of N, S, or O and optionally substituted by hydroxy, alkanoyloxy, primary, secondary, or tertiary amino, amino($C_{1-4}$)alkyl, mono- or di($C_{1-4}$) alkyl-amino(C1-4)alkyl, halogen, ($C_{1-4}$)alkyl, and tri ($C_{1-4}$)alkylammonium($C_{1-4}$)alkyl;

∿∿∿ is a chain of 1 to 5 carbon atoms optionally containing a double bond or a NR' group wherein R' is hydrogen or ($C_{1-4}$) alkyl;

R is hydrogen or phenyl;

X is an oxygen atom or a NR' group wherein R' is hydrogen or ($C_{1-4}$)alkyl or is absent;

r and m are independently 0, 1, or 2;

B is a phenylene or cyclohexylene ring;

Y is hydroxy;

with the proviso that a tricyclic group as defined for A is fluorenyl only when said fluorenyl is substituted by a tri($C_{1-4}$)alkylammonium($C_{1-4}$)alkyl group.

2. The compound of claim 1, wherein A is selected from phenyl, 1- or 2-naphthyl, cyclohexyl, 1,2,3,4-tetrahydronaphth-1- or -2-yl, adamantyl, quinolinyl, isoquinolinyl, 1- or 2-indenyl, tetrahydroquinolinyl, tetrahydroisoquinolinyl optionally substituted;

∿∿∿ is a $C_1$–$C_5$ chain;

and R, B, m and r are as defined in claim 1.

3. The compound of claim 1, wherein A is optionally substituted phenyl or 1- or 2-naphthyl.

4. A method of treating Inflammation which comprises administering to a patient in need of such treatment a compound of claim 1 in an amount effective to provide an anti-inflammatory effect.

5. A method of suppressing immune response which comprises administering to a patient in need of such treatment a compound of claim 1 in an amount effective to provide an immunosuppressive effect.

6. A pharmaceutical composition containing as the active ingredient an effective amount of a compound of claim 1 together with pharmaceutically acceptable excipient.

7. The compound of claim 1 identified as 4-(5-phenylpentanamido)benzohydroxamic acid.

8. The compound of claim 1 selected from the group consisting of 4-{2,2-(diphenyl) ethoxycarbamoylmethyl}benzohydroxamic acid and 4-{3,3-(diphenyl)propoxycarbamoyl}benzohydroxamic acid.

9. The compound of claim 1 identified as 4-{2-adamant-1-yl)-ethoxycarbamoyl}benzohydroxamic acid.

10. The compound of claim 1 selected from the group consisting of 4-{(naphth-1-yl)

methoxycarbamoyl}benzohydroxamic acid, 4-{(naphth-2-yl)methoxycarbamoyl}benzohydroxamic acid, and 4-{(1,2,3,4-tetrahydronaphth-2-yl)methoxycarbamoyl}benzohydroxamic acid.

11. The compound of claim 1 identified as 4-{(3-phenylpropoxy)carbamoyl}benzohydroxamic acid.

12. The compound of claim 1 identified as 4-{(3-phenylprop2-enyl)carbamoyl}benzohydroxamic acid.

13. The compound of claim 1 selected from the group consisting of 4-{6-(diethylaminomethyl)naphth-2-ylmethyloxycarbamoyl}benzohydroxamide acid, 4-{6-(dipropylaminomethyl)naphth-2-ylmethyloxycarbamoyl}benzohydroxamic acid, 4-{6-(dibutylaminomethyl)naphth-2-ylmethyloxycarbamoyl}benzohydroxamic acid, and 4-{4(diethylaminomethyl)naphth-1-ylmethyloxycarbamoyl}benzohydroxamide acid.

14. The compound of claim 1 identified as 4-{6-(diethylaminomethyl)naphth-2-ylmethylaminocarbamoyl}benzohydroxamic acid.

15. The compound of claim 1 identified as 4-{N-isopropyl-1,2,3,4-tetrahydroisoquinol-3-yl)methyloxycarbamoylmethyl}benzohydroxamic acid.

* * * * *